United States Patent
Gros et al.

(10) Patent No.: US 10,792,401 B2
(45) Date of Patent: Oct. 6, 2020

(54) MEDICAL EXAMINATION GLOVES

(71) Applicant: Chemical Intelligence Limited, Shropshire (GB)

(72) Inventors: Robert Gros, London (GB); Paul Wight, Chorlton Manchester (GB)

( * ) Notice: Subject to any disclaimer, the term of this patent is extended or adjusted under 35 U.S.C. 154(b) by 56 days.

(21) Appl. No.: 16/081,629

(22) PCT Filed: Feb. 28, 2017

(86) PCT No.: PCT/EP2017/054662
§ 371 (c)(1),
(2) Date: Aug. 31, 2018

(87) PCT Pub. No.: WO2017/148957
PCT Pub. Date: Sep. 8, 2017

(65) Prior Publication Data
US 2019/0083684 A1    Mar. 21, 2019

(30) Foreign Application Priority Data

Mar. 1, 2016  (EP) .................................... 16158134

(51) Int. Cl.
| | | |
|---|---|---|
| A41D 31/30 | (2019.01) | |
| A61L 31/16 | (2006.01) | |
| A61L 31/12 | (2006.01) | |
| A61L 31/04 | (2006.01) | |
| A41D 19/00 | (2006.01) | |
| B29C 41/14 | (2006.01) | |
| C08K 3/36 | (2006.01) | |
| C08K 5/1545 | (2006.01) | |
| C08K 5/544 | (2006.01) | |
| C08L 9/02 | (2006.01) | |
| A61B 42/10 | (2016.01) | |
| B29K 7/00 | (2006.01) | |

(52) U.S. Cl.
CPC ........ *A61L 31/128* (2013.01); *A41D 19/0058* (2013.01); *A41D 31/30* (2019.02); *A61L 31/049* (2013.01); *A61L 31/125* (2013.01); *A61L 31/16* (2013.01); *B29C 41/14* (2013.01); *C08K 3/36* (2013.01); *C08K 5/1545* (2013.01); *C08K 5/544* (2013.01); *C08L 9/02* (2013.01); *A41D 2600/20* (2013.01); *A61B 42/10* (2016.02); *A61L 2300/404* (2013.01); *B29K 2007/00* (2013.01); *C08K 2201/011* (2013.01)

(58) Field of Classification Search
None
See application file for complete search history.

(56) References Cited

U.S. PATENT DOCUMENTS

| | | | |
|---|---|---|---|
| 6,361,786 B1 * | 3/2002 | Shanbrom | A61F 13/36 424/405 |
| 2012/0148651 A1 * | 6/2012 | Amdur | A01N 25/34 424/409 |
| 2019/0083684 A1 * | 3/2019 | Gros | C08K 5/1545 |

FOREIGN PATENT DOCUMENTS

WO    WO 2007/062306    5/2007

OTHER PUBLICATIONS

Written Opinion of the International Searching Authority for PCT/EP2017/054662, filing date Feb. 28, 2017. (6 pgs).

* cited by examiner

*Primary Examiner* — Peter A Salamon
(74) *Attorney, Agent, or Firm* — Finnegan, Henderson, Farabow, Garrett & Dunner, LLP

(57) ABSTRACT

The disclosed medical examination glove comprises natural or nitrile rubber latex, and a water soluble singlet oxygen generator. The glove can be manufactured by contacting a glove former with a coagulant solution comprising divalent calcium cations and carbonate particles and a water soluble singlet oxygen generator and then contacting the glove former with a natural or nitrile rubber latex dispersion.

19 Claims, No Drawings

MEDICAL EXAMINATION GLOVES

CROSS-REFERENCE TO RELATED PATENT APPLICATIONS

This application is a National Stage Entry of International Application No. PCT/EP2017/054662, filed Feb. 28, 2017, which claims priority from EP Application No. 16158134.3, filed Mar. 1, 2016. The entire contents of the above-referenced applications are expressly incorporated herein by reference.

FIELD OF INVENTION

The present invention relates to medical examination gloves, a method for manufacturing medical examination gloves, and medical examination gloves obtainable by the method.

BACKGROUND ART

Medical gloves are disposable gloves used during medical examinations and procedures that help prevent the spread of infections. There are two distinct types of medical gloves: medical examination gloves and surgical gloves. Due to the precision required in surgical operations, the sizes of surgical gloves are more precise, have greater sensitivity, and are made to a higher standard. Therefore, for the two types of medical gloves the methods of manufacture are different.

Medical gloves can be made from a selection of different polymers and come un-powdered or powdered with cornstarch to lubricate the gloves, making them easier to put on the hands. Cornstarch replaced tissue irritating Lycopodium powder and talc, but since even cornstarch can impede healing if it gets into tissues, as during surgery, un-powdered gloves are being used more often during surgery and other sensitive procedures. Special manufacturing processes are used to compensate for the lack of powder. Examination gloves are non-powdered.

Gloves that have been sterilized are free of microbiological contamination including bacteria. Sterile gloves are necessary for all surgical procedures and other medical purposes where there is a greater risk and danger from infection. Sterile gloves are packaged in pairs inside sterile pouches with their own sterile field. In comparison, non-sterile gloves are packaged in boxes of 100 or 200 pairs and are used in everyday common medical activities. Glove usage in hospitals is primarily therefore non-powdered and non-sterile.

Due to their low cost, disposable polyvinyl chloride (PVC) latex gloves are the most economical gloves for cost conscious facilities. These examination gloves provide standard bather protection. In addition to being comfortable to wear, vinyl gloves have a soft feel. For a great value allergen-free choice, PVC latex examination gloves are the favourable option. However, they are less durable, have lower elongation, and there is a bad perception of them.

In general, PVC latex gloves are not textured because the raw material (PVC) does not make manufacturing textured gloves easy.

Sterile examination gloves are available that come in individual packaging, but the gloves only remain sterile until the pack is opened, after which they can pick up infections.

Examination gloves are used by medical staff to prevent the transfer of infections between medical workers and their patients. They are worn by medical workers at the start of the examination and discarded and destroyed at the end of the procedure. They function by creating a physical barrier between the medical practitioner and patient that prevents the transfer of infectious microorganisms between the two parties. The gloves themselves are not sterile and there is always a danger that the gloves could tear, allowing microorganisms to be transferred between the patient and the practitioner.

US2011/0145975 describes how to coat gloves with an anti-bacterial agent. To get the outside of the glove coated, they have to do the coating in an "offline process", by completing the glove preparation, stripping it from the glove former, then placing it in a tumble dryer equipped with sprayers which coat the glove with the anti-bacterial agent, and then carry out a polymer coating. The polymer coating is required because the anti-bacterial agent is sticky, so there is a need to coat the glove with something to make it usable. Disadvantages of this process are that the anti-bacterial agent is carcinogenic, and does not stay on the gloves, as it leaches off them in use. It also adds a separate process to the manufacturing.

SUMMARY OF THE INVENTION

The present invention provides medical examination glove comprising:
  a) natural or nitrile rubber latex;
  and
  b) a water soluble singlet oxygen generator.

The present invention further provides method of manufacturing a natural or nitrile rubber latex medical examination glove, comprising:
  (a) contacting a glove former with a coagulant solution comprising divalent group 2 metal cations and carbonate particles and a water soluble singlet oxygen generator;
  and
  (b) contacting the glove former with a natural or nitrile rubber latex dispersion.

The present invention also provides medical examination gloves obtainable by the method of the present invention.

The medical examination gloves of the present invention are antimicrobial and can themselves kill infectious microorganisms on the glove, on the hand of the wearer, and on any medical equipment or on parts of the patient touched by the medical expert's gloved hands. The antimicrobial properties of the glove ensure that infection cannot be transferred even if the glove suffers small tears and if the physical barrier is breached. The method of manufacture is suitable for examination gloves, rather than surgical gloves.

DETAILED DESCRIPTION OF THE INVENTION

Gloves

Natural Rubber Latex

Natural rubber lattices can be obtained from the sap of rubber trees. Although concerns regarding latex allergies continue, natural rubber latex gloves are unsurpassed when it comes to durability, tactile sensitivity, comfort and fit. The advantages are high tactile sensitivity, being very durable and comfortable. The disadvantages are that they are dry, and that allergy to the proteins in the natural rubber latex irritates the skin.

Nitrile Rubber Latex

Nitrile rubber can be made synthetically by co-polymerising acrylonitrile and butadiene. Due to their resilience, nitrile rubber gloves work very well in harsh, high-stress environments. Nitrile rubber synthetic examination gloves provide excellent protection against a wide range of chemicals in addition to being an effective barrier against blood-borne pathogens. They provide excellent barrier protection and chemical resistance. Most importantly, nitrile rubber latex is allergen-free and provides three times more puncture resistance than standard natural rubber latex examination gloves.

Around 6% of the general population have latex allergy and as many as 17% of health care workers are reported to be affected. Replacing natural rubber latex gloves with nitrile rubber latex gloves will help make the clinical environment safer for staff and patients with latex allergies without sacrificing the quality of the gloves.

Preferably therefore, the examination gloves of the present invention comprise nitrile rubber.

Preferably the natural rubber latex or nitrile rubber latex gloves are textured, rather than smooth, to prevent slippage especially when handling moist or wet objects. Preferably glove thickness is in the range of 20 to 100 μm for optimal grip.

or monomeric cationic species such as quaternary ammonium salts, which themselves may be biocides, such as Lonzabac GA.

The singlet oxygen generators may also be bound to inorganic nanoparticles. The nanoparticles should preferably have the complementary charge to the singlet oxygen generator. Methylene blue can be used with cationically modified silica nanoparticles such as Ludox CL and anionic singlet oxygen generators can be bound to anionic silica nanoparticles such as Ludox SM, or Ludox HS-30. The anionic silica nanoparticles are preferred to be used in the latex.

Biocide

It is further preferred that the singlet oxygen generators are used in combination with a biocide. Preferably, the biocide is selected from the group comprising chlorohexidene triclosan, benzalkonium chloride, silver salts and nanoparticles, poly(hexamethylene biguanide) (PHMB), peroxides, and more preferably surface reactive biocide Dimethyloctadecyl[3-(trimethoxysilyl)propyl]ammonium chloride, shown below:

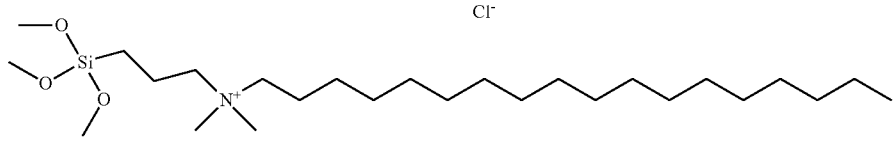 [SMILES: [Cl-] ; CCCCCCCCCCCCCCCCCC[N+](C)(C)CCC[Si](OC)(OC)OC]

Singlet Oxygen Generator

The singlet oxygen generators in the present invention are permanently water soluble. This is made possible for example by virtue of having a charged group, such as carboxylate, sulphonic acid, or ammonium. The singlet oxygen generators can be selected for quantum efficiency, binding to the surface of latex, stability and toxicity. The singlet oxygen generators are preferably stable and/or soluble in high strength group 2 metal solutions, preferably calcium solutions, efficient generators at moderate light levels, and do not interfere with the other properties of the latex.

The present inventors have found that addition of these substances destroys microorganisms brought in contact with the material of the glove. The singlet oxygen generators can be used alone or in combination. It is preferred that a combination of singlet oxygen generators is used, and especially that the combination of singlet oxygen generators which absorb different wavelengths of light, such as a red singlet oxygen generator combined with a blue singlet oxygen generator, so as to maximise the amount of singlet oxygen generated by a given incidence of light intensity.

Certain classes of dyes are known to generate singlet oxygen in the presence of ground state tripet oxygen on illumination with light. These have use in photodynamic therapy, and also may have biocidal properties.

Examples of singlet oxygen generators include Methylene Blue, Rose Bengal, Tinolux BBS, Tinolux BMC, or other phthalocyanine compounds made water soluble by containing ionic groups.

It is preferred that the water soluble singlet oxygen generators are fixed, by making an ion pair with an cationic material, such as polyethylenimine, or PHMB, in order to prevent their migration through the latex.

The singlet oxygen generators may also be combined with cationic fixing agents, such as polyethylene imine, PHMB, The singlet oxygen generators can also be combined with other biocides, such as those disclosed in WO2013167850 A1.

Manufacturing Method

The method comprises contacting a glove former with a coagulant solution comprising divalent group 2 metal cations and optionally group 2 metal carbonate or stearate particles, preferably calcium cations and calcium carbonate particles, and a water soluble singlet oxygen generator, and then contacting the glove former with a natural or nitrile, preferably nitrile, rubber latex dispersion. Calcium ions cause the latex particles to form a film. The carbonate or stearate particles act as a mold release and make it easier to remove cured latex film from the former.

The formers on which the gloves form can be mounted on a continuous conveyor belt that takes the formers through a series of dip tanks and ovens. The dip tanks, into which the formers are submerged, may be continually fed with fresh solution to replace solution that is removed when the coated formers leave the tank. In addition the solution in each tank may be continuously circulated to ensure that its composition remains uniform. Biocides in a solution concentrate can be metered into the tank along with the regular make up solution. The composition of the solution concentrate added to the coagulation tank is different from the concentrate added to the natural or nitrile rubber dipping tank.

The conditions employed are variable depending on glove type and thickness. Preferably, a former at a temperature in the range of 60 to 150° C. is dipped in coagulant at a temperature in the range of 40 to 70° C., for a period in the range of two to ten seconds. It can then be dried at a temperature in the range of 100 to 160° C. for a period in the range of one to ten minutes. Then it can be dipped in latex for a period of one to ten seconds and cured at a temperature in the range of 70 to 150° C. for a period of ten to forty minutes.

First Stage

Clean porous porcelain glove formers, mounted on a continuous conveyor belt, can be dipped into a tank containing a coagulant solution containing multivalent such as calcium ions and possibly a particulate solid such as calcium carbonate.

Preferably singlet oxygen generators are compatible with and are added to the coagulant solution. The singlet oxygen generators in the present invention are permanently water soluble for example by virtue of having a charged group, such as carboxylate, sulphonic acid, or ammonium. The singlet oxygen generators can be selected for quantum efficiency, binding to the surface of latex, stability, toxicity.

Examples of such singlet oxygen generators include Methylene Blue, Rose Bengal, Tinolux BBS, Tinolux BMC, or other phthalocyanine compounds made water soluble by containing ionic groups, and especially cationic phthalocyanine singlet oxygen generators, more especially zinc or aluminium phthalocyanines made water soluble by bearing cationic groups.

The singlet oxygen generators can be used alone or in combination. If in combination, a mixture of different colours, e.g. a red and a blue dye are preferred, so that they use more of the available spectrum of white light.

Preferably, the singlet oxygen generators can be combined with cationic fixing agents, such as polyethylene imine, PHMB, or monomeric cationic species such as quaternary ammonium salts, which themselves may be biocides, such as Lonzabac GA.

The singlet oxygen generators can also be dipped or sprayed into the former first, with the fixing agent in the coagulant bath. Alternatively, the fixing agent can be pre-dipped onto the former, with the singlet oxygen generators in the coagulant bath.

The singlet oxygen generators can also be bound to inorganic nanoparticles. The nanoparticles preferably should have the complementary charge to the singlet oxygen generator, so that they bind to them in the coagulant bath. Methylene blue can be used with cationically modified silica nanoparticles such as Ludox CL (from Grace inc.) and anionic singlet oxygen generators can be bound to anionic silica nanoparticles such as Ludox SM, or Ludox HS-30. The anionic silica nanoparticles are preferred to be used in the latex.

A surface reactive biocide can also be incorporated into the coagulant bath, such as Dimethyloctadecyl[3-(trimethoxysilyl)propyl]ammonium chloride.

It is preferred that the water soluble singlet oxygen generators are fixed, by making an ion pair with an cationic material, such as polyethylenimine, or PHMB, in order to prevent their migration through the latex in the manufacturing process.

The singlet oxygen generators can also be added to the latex dipping bath, alone or in combination with biocides known in the art, such as those disclosed in WO2013167850 A1.

The method of the present invention ensures uniformed distribution of antibacterial agents using an ionic solution, and enables the antimicrobial agents to be added to the coagulant solution and to physically and chemically bond the active ingredients uniformly to the surface of the rubber latex gloves.

The quantities of each constituent can range from 0.0001% up to 1% of each active ingredient in the coagulant. Careful design of the composition of the antimicrobial blend ensures the continued smooth operation of the manufacturing process, preventing the active ingredients from coming into contact with the ingredients in the nitrile rubber latex and the uniform incorporation of the antimicrobial agents on to the surface of the glove.

Second Stage

The formers can be withdrawn from the solution and drained before passing through an oven in which the coagulant solution adhering to the formers dries.

Third Stage

The former, with dried coagulant on its surface may be dipped into the tank containing an aqueous nitrile or natural rubber latex suspension blended with other additives as required. Anionic nitrile rubber latex particles in the vicinity of the cationic surface of the former coagulate can be deposited on the former in a thin layer.

Fourth Stage

The nitrile rubber latex coated former can be lifted out of the nitrile rubber solution, allowed to drain, and then passes through another oven. Heating the coagulated nitrile rubber latex particles on the former evaporates the water and causes the polymer particles to coalesce and form a continuous polymer film that is the glove.

Fifth Stage

The formed glove can undergo further treatment processes, including beading. The glove may then be removed from the former with a sharp blast of compressed air. This process turns the gloves "inside out", the surface of the glove on the porcelain former, in contact with the calcium coagulant suspension, becomes the outer surface of the glove.

Sixth Stage

The former can be cleaned and then returned to the coagulation tank to repeat the cycle.

Incorporation of Biocidal Agents

The present inventors have developed a process that can incorporate a synergistic mixture of biocidal agents into the glove by adding a specially formulated mixture of biocides into the calcium coagulant suspension and/or the nitrile or natural rubber compound suspension. The composition of both suspensions is preferably very carefully controlled to ensure that they perform as required. The coagulant suspension preferably remains stable, to deposit coagulant ions and calcium carbonate particles onto the surface of the clean former. The nitrile or natural latex rubber suspension can then deposit the layer of coagulated nitrile rubber latex particles onto the glove former. Certain ingredients might cause either suspension to coagulate without coming into contact with the former.

Incorporating the biocide onto the outside surface of the glove will prevent the glove picking up an infection and infecting the patient. Biocide incorporated into the natural latex or nitrile rubber layer will also protect the wearer against the danger of the glove tearing.

The present inventors have identified particular antibacterial agents, as described above, and ways of incorporating them into the glove that will protect both their wearer and their patient from the dangers of cross infections. A wide range of antibacterial agents have been evaluated and found to be effective. These include singlet oxygen generator and surface reactive biocidal agents.

One or more of the following antibacterial agents can added to the calcium coagulant suspension: Methylene Blue, Rose Bengal, Tinolux BMC, Tinolux BBS, Poly(hexamethylene biguanide) (PHMB), Chlorohexidene, Benzalkonium chloride such as BTC 50E, Triclosan, Dimethyloctadecyl[3-(trimethoxysilyl)propyl]ammonium chloride.

In addition, one or more of the following fixing agents and adjuvants can be added to the coagulant bath: Ludox CL silica nanoparticles (in combination with anionic singlet oxygen generators); water soluble compounds containing a methyl substituted vinyl group that can react with singlet oxygen to produce a peroxide, such as geraniol, prenol or nerol; cationic polymers such as polyethylene imine; anionic polymers where these are stable to calcium nitrate, such as polystyrene sulphonate and polymethacryclic acid.

One or more of the following anti-bacterials can be added to the nitrile rubber latex suspension: Triclosan, BIT. 1,2-Benzisothiazol-3((2H)-one, such as Proxil; Phenoxyethanol; Methylchloroisothiazolinone; Rose Bengal; Methylene Blue; Tinolux BMC; Tinolux BBS.

In addition one or more of the following fixing agents and adjuvants can be added to the coagulant bath: Ludox silica nanoparticles such as Ludox HS-30, or Ludox SM in combination with cationic singlet oxygen generators; water soluble compounds containing a methyl substituted vinyl group that can react with singlet oxygen to produce a peroxide, such as geraniol, prenol or nerol; anionic polymers such as polystyrene sulphonate and polymethacryclic acid.

The present invention therefore provides:
1. A medical examination glove comprising:
   a) natural or nitrile rubber latex; and
   b) a water soluble singlet oxygen generator.
2. The glove according to 1, wherein the singlet oxygen generator is selected from the group comprising xanthenes, preferably Rose Bengal, thiazones, preferably Methylene Blue or Toluidine Blue, and water soluble phthalocyanines, preferably Tinolux BBS or Tinolux BMC, or especially cationic phthalocyanine singlet oxygen generators.
3. The glove according to 1 or 2, comprising a mixture of red and blue singlet oxygen generators.
4. The glove according to any preceding, further comprising a biocide.
5. The glove according to 4, wherein the biocide is selected from the group comprising chlorohexidene triclosan, benzalkonium chloride, silver salts and nanoparticles, poly(hexamethylene biguanide) (PHMB), an organic peroxide or hydroperoxide, and preferably surface reactive biocide Dimethyloctadecyl[3-(trimethoxysilyl)propyl]ammonium chloride.
6. The glove according to any preceding, further comprising a dye, preferably a combination of red and blue dyes.
7. The glove according to any preceding, wherein the singlet oxygen generator is bound to inorganic nanoparticles, preferably cationically modified silica nanoparticles.
8. The glove according to any preceding, further comprising polymeric or monomeric organic cations, preferably polyethylene imine or PHMB.
9. The glove according to any preceding, further comprising polymeric or monomeric anions, preferably polystryene sulphonate, or polymethacyrilic acid.
10. A method of manufacturing a natural or nitrile rubber latex medical examination glove, comprising:
    (a) contacting a glove former with a coagulant solution comprising divalent group 2 metal cations and optionally carbonate or stearate particles, and a water soluble singlet oxygen generator; and
    (b) contacting the glove former with a natural or nitrile rubber latex dispersion.
11. The method according to 10, wherein the singlet oxygen generator is selected from the group comprising xanthenes, preferably Rose Bengal, thiazones, preferably Methylene Blue or Toluidine Blue, and water soluble phthalocyanines, preferably Tinolux BBS or Tinolux BMC, more prefereably cationic phthalocyanine singlet oxygen generators.
12. The method according to 10 or 11, comprising a mixture of red and blue singlet oxygen generators.
13. The method according to any of 10 to 12, wherein the coagulant solution further comprises a biocide.
14. The method according to any of 10 to 13, wherein the biocide is selected from the group comprising chlorohexidene triclosan, benzalkonium chloride, silver salts and nanoparticles, poly(hexamethylene biguanide) (PHMB), and preferably surface reactive biocide Dimethyloctadecyl[3-(trimethoxysilyl)propyl]ammonium chloride.
15. The method according to any of 10 to 14, wherein the coagulant solution further comprises a dye, preferably a combination of red and blue dyes.
16. The method according to any of 10 to 15, wherein the singlet oxygen generator is bound to inorganic nanoparticles, preferably cationically modified silica nanoparticles.
17. The method according to any of 10 to 16, wherein the coagulant solution further comprises a water soluble methyl substituted vinyl compound, preferably including gereniol, prenol or nerol.
18. The method according to any of 10 to 17, wherein polymeric or monomeric organic cations are present, preferably polyethylene imine or PHMB.
19. The method according to any of 10 to 18, wherein inorganic cationic nanoparticles are present, preferably cationically modified silica nanoparticles.
20. The method according to any of 10 to 19, wherein polymeric or monomeric organic anions are present, preferably polystyrene sulphonate or polymethacyrilic acid.
21. The method according to any of 10 to 20, wherein cationic singlet oxygen generators are present in the coagulant solution and anionic singlet oxygen generators are present in the latex dispersion.
22. The method according to any of 10 to 20, wherein anionic singlet oxygen generators are present in the coagulant solution and cationic singlet oxygen generators are present in the latex dispersion.
23. The method according to any of 10 to 22, wherein the glove former is pre-contacted with cationic fixing agents and then contacted with the coagulant solution, said fixing agents preferably selected from the group comprising polyamines or polyquats, or monometic cationic fixing agents, preferably polyethylene imine, PHMB or Vantocil IB.
24. The method according to any of 10 to 22, wherein the glove former is pre-contacted with anionic single oxygen generators and then contacted with the coagulant solution further comprising cationic fixing agents, preferably polyamines or polyquats, or monometic cationic fixing agents, preferably polyethylene imine or PHMB.
25. A medical examination glove obtainable by the method according to any of 10 to 24.

Vinyl latex can also be used instead of or with nitrile or natural rubber latex for 1 to 25.

The present invention will now be illustrated, but in no way limited, by reference to the following examples.

EXAMPLES

Tests were carried out in order to assess which combination of biocidal agents were compatible with the glove manufacturing process and gave the best antimicrobial performance. Small rectangles of nitrile rubber latex were prepared by dipping clean microscope slides into warm coagulant solution, withdrawing them and drying them in an oven at 110° C. The slides were allowed to cool before dipping into the nitrile rubber latex dispersion. They were withdrawn, allowed to drain, and placed in an oven at 110° C. After cooling the layer of cured nitrile rubber was carefully removed from the microscope slide and sent for testing to determine their antimicrobial properties. Active ingredients were incorporated into the coagulant and nitrile polymer latex dispersion as appropriate.

The antibacterial performance of the produced gloves can be measured by established methods known in the art, such as ASTM D7907, ASTM E2149 or other known methods to determine the antibacterial activity of surfaces.

Example 1

0.6 parts of Rose Bengal and 30 parts of a 10% solution of Tinolux BMC (BASF) were dissolved with stirring in 70 parts of water. This solution was added to 6000 parts of a standard coagulant bath made up of 17% by weight of calcium nitrate. Gloves were then made by the process described above.

Example 2

A latex containing SOG was made by adding 3.6 parts of Rose Bengal to a standard nitrile latex containing 18% latex by weight. 4 parts of Rewocid WK30 (ex Brentag ltd), 20 parts of Teric (10%) (need suppliers), and 58 parts of water were stirred to solution. 18 parts of Dimethyloctadecyl[3-(trimethoxysilyl)propyl]ammonium chloride in methanol 72% by weight (AEM 5772 from Devan Chemicals pvt) were stirred in to give a clear solution. This was added to 6000 parts of standard coagulant bath containing 17% by weight of calcium nitrate. The formers were dipped in the coagulant bath, and after drying in the oven, as per the process above, were dipped in the latex prepared containing the Rose Bengal.

Example 3

16 parts of AEM 5772 were stirred into 50 parts of water containing 35 parts of Teric (10% solution). This was added to 6000 parts of standard coagulant bath containing 17% calcium nitrate. Gloves were made using this coagulant bath as per the process described above.

Example 4

16 parts of AEM 5772 were stirred into 50 parts of water containing 35 parts of Teric (10% solution). This was added to 6000 parts of standard coagulant bath containing 17% calcium nitrate. 0.6 parts of Rose Bengal dissolved in 25 v parts of water were added to the coagulant bath. Gloves were made using this coagulant bath as per the process described above.

Results

The table below shows the log reduction in Staphylococcus Aureus after 6 minutes as measured by ASTM D7907, Method A.

| Example | Log Reduction |
| --- | --- |
| 1 | 3.64 |
| 2 | 5.27 |
| 3 | 0.3 |
| 4 | 5.27 |

The invention claimed is:

1. A medical examination glove comprising natural rubber latex or nitrile rubber latex and at least one water-soluble singlet oxygen generator, wherein the at least one singlet oxygen generator is present with at least one fixing agent or bound to at least one inorganic nanoparticle, wherein the glove further comprises polymeric or monomeric anions selected from the group consisting of polystyrene sulphonate and polymethacrylic acid.

2. The glove according to claim 1, wherein the at least one singlet oxygen generator is selected from the group consisting of xanthenes, thiazones and water soluble phtalcocyanine singlet oxygen generators.

3. The glove according to claim 2, wherein the at least one singlet oxygen generator is selected from the group consisting of rose bengal, methylene blue, toluidine blue, tinolux BBS, tinolux BMC, and cationic phthalocyanine singlet oxygen generator.

4. The glove according to claim 2, wherein the singlet oxygen generator is a mixture of red and blue singlet oxygen generators.

5. The glove according to claim 1, wherein the at least one inorganic nanoparticle comprises cationically modified silica nanoparticles.

6. The glove according to claim 1, further comprising a biocide selected from the group comprising chlorohexidene triclosan, benzalkonium chloride, silver salts and nanoparticles, poly(hexamethylene biguanide) (PHMB), organic peroxide or hydroperoxide, and dimethyloctadecyl[3-(trimethoxysilyl)propyl]ammonium chloride.

7. The glove according to claim 1, further comprising polymeric or monomeric organic cations selected from the group comprising polyethylene imine or PHMB.

8. A method of manufacturing a natural or nitrile rubber latex medical examination glove, comprising:
(a) contacting a glove former with a coagulant solution, wherein the coagulant solution comprises divalent group 2 metal cations, polymeric or monomeric anions selected from the group consisting of polystyrene sulphonate and polymethacrylic acid, and at least one water-soluble singlet generator is present with at least one fixing agent or bound to inorganic nanoparticles; and
(b) contacting the glove former with a natural or nitrile rubber latex dispersion.

9. The method according to claim 8, wherein the coagulant solution further comprises carbonate or stereate particles.

10. The method according to claim 8, wherein the at least one singlet oxygen generator is selected from the group consisting of rose bengal, methylene blue, toluidine blue, Tinolux BBS and Tinolux BMC.

11. The method according to claim 8, wherein the at least one singlet oxygen generator is a mixture of red and blue singlet oxygen generators.

12. The method according to claim 8, wherein the coagulant solution further comprises a biocide selected from the group comprising chlorohexidene triclosan, benzalkonium chloride, silver salts and nanoparticles, poly(hexamethylene biguanide) (PHMB), organic peroxide or hydroperoxide, and dimethyloctadecyl[3-(trimethoxysilyl)propyl]ammonium chloride.

13. The method according to claim 8, wherein the coagulant solution further comprises a water soluble methyl substituted vinyl compound selected from gereniol, prenol or nerol.

14. The method according to claim 8, wherein the coagulant solution further comprises polymeric or monomeric organic cations selected from the group comprising polyethylene imine or PHMB.

15. The method according to claim 8, wherein the coagulant solution comprises cationic singlet generators, and the latex dispersion comprises anionic singlet oxygen generators.

16. The method according to claim 8, wherein the coagulant solution comprises anionic singlet generators, and the latex dispersion comprises cationic singlet oxygen generators.

17. The method according to claim 8, wherein the glove former is contacted with a cationic fixing agent prior to it being contacted with the coagulant solution, and wherein the cationic fixing agent is selected from the group comprising polyamines or polyquats, or monometic cationic fixing agents, preferably polyethylene imine, PHMB and Vantocil IB.

18. The method according to claim 8, wherein the glove former is pre-contacted with anionic single oxygen generators and then contacted with the coagulant solution further comprising cationic fixing agents or monomeric cationic fixing agents, and further wherein the cationic fixing agents are selected from polyamines or polyquats, and the monomeric cationic fixing agents are selected from polyethylene imine or PHMB.

19. The glove according to claim 8, wherein the at least one inorganic nanoparticle comprises cationically modified silica nanoparticles.

* * * * *